US012708923B2

(12) United States Patent
Lee et al.

(10) Patent No.: US 12,708,923 B2
(45) Date of Patent: Aug. 18, 2026

(54) MESH TYPE ATOMIZER USING POROUS THIN FILM AND METHOD FOR MANUFACTURING THE SAME

(71) Applicant: KOREA INSTITUTE OF SCIENCE AND TECHNOLOGY, Seoul (KR)

(72) Inventors: Byung Chul Lee, Seoul (KR); Dong-Hyun Kang, Seoul (KR); Shinyong Shim, Seoul (KR); Dong Jun Kim, Seoul (KR); Jin Soo Park, Seoul (KR); Ki Joo Pahk, Seoul (KR); Hyejeong Seong, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 1308 days.

(21) Appl. No.: 17/412,265

(22) Filed: Aug. 26, 2021

(65) Prior Publication Data

US 2022/0234301 A1 Jul. 28, 2022

(30) Foreign Application Priority Data

Jan. 25, 2021 (KR) ........................ 10-2021-0010201

(51) Int. Cl.
*B05B 17/00* (2006.01)
*A61M 11/00* (2006.01)

(52) U.S. Cl.
CPC ....... *B05B 17/0646* (2013.01); *A61M 11/003* (2014.02); *A61M 11/005* (2013.01)

(58) Field of Classification Search
CPC ..... B05B 1/26; B05B 17/0646; B23K 26/362; A61M 11/003; A61M 11/005;
(Continued)

(56) References Cited

U.S. PATENT DOCUMENTS 3,790,079 A * 2/1974 Berglund ............ B05B 17/0607 366/115
8,616,195 B2 * 12/2013 Power ................. B05B 17/0607 128/200.14
(Continued)

FOREIGN PATENT DOCUMENTS

CN 202823727 U 3/2013
CN 210474459 U 5/2020
(Continued)

OTHER PUBLICATIONS

Chunjin Hang et al., "A Modified Interposer Fabrication Process by Copper Nano-Pillars Filled in Anodic Aluminum Oxide Film for 3D Electronic Package," Applied Sciences, 2018, 10 pages, vol. 8, No. 2188.
(Continued)

*Primary Examiner* — Woody A Lee, Jr.
(74) *Attorney, Agent, or Firm* — CANTOR COLBURN LLP

(57) ABSTRACT

A mesh type atomizer according to an embodiment includes a porous thin film having a multi-hole structure, a metal layer covering a remaining area except a nozzle area in which droplets are sprayed through the holes on a surface of the porous thin film, and an ultrasonic transducer to output ultrasonic waves to vibrate the porous thin film. According to an embodiment, it is possible to atomize a liquid into nanometer-level fine particles using the porous thin film including nanometer sized holes. It is possible to precisely adjust the sprayed droplet size by setting the shape, size and cycle of the nozzle in the manufacturing process, and it is possible to selectively increase the strength of the mesh by growing the metal material in the hole of the porous thin film through electroplating.

9 Claims, 10 Drawing Sheets

(58) Field of Classification Search
CPC .. A61M 2205/0211; A61M 2205/0238; A61M 15/0085; A61M 2207/00; B29C 66/71; B29C 65/16; C25D 11/04
USPC .................................................... 219/121.76
See application file for complete search history.

(56) References Cited

U.S. PATENT DOCUMENTS

| | | | | |
|---|---|---|---|---|
| 2011/0314933 | A1* | 12/2011 | Mueller | G10K 11/004 29/25.35 |
| 2012/0038248 | A1* | 2/2012 | Mueller | G01F 1/667 310/337 |
| 2016/0051226 | A1* | 2/2016 | Hong | B06B 1/0292 600/459 |
| 2019/0362118 | A1* | 11/2019 | Ahn | G06V 40/1306 |

FOREIGN PATENT DOCUMENTS

| | | | |
|---|---|---|---|
| CN | 212466765 | U | 2/2021 |
| EP | 3476982 | A1 | 5/2019 |
| JP | 60-68071 | A | 4/1985 |
| JP | 6415953 | B2 | 10/2018 |
| KR | 10-0958663 | B1 | 5/2010 |
| KR | 10-2017-0137431 | A | 12/2017 |
| WO | 2017/209336 | A1 | 12/2017 |

OTHER PUBLICATIONS

The extended European Search Report for EP Application No. 21193052.4 mailed on Feb. 2, 2022.

* cited by examiner

MESH TYPE ATOMIZER USING POROUS THIN FILM AND METHOD FOR MANUFACTURING THE SAME

DESCRIPTION OF GOVERNMENT-FUNDED RESEARCH AND DEVELOPMENT

This research is conducted by Korea Institute of Science and Technology under the support of collaborative life-cycle medical device R&D project (Development of capacitive micromachined ultrasonic transducer for MR-compatible functional multimodal imaging and treatment: 2M35810) of the Ministry of Trade, Industry and Energy and innovation challenge pilot project (Development of ultrasonic probe and attachable device using semiconductor technology. Project Series No.: 2N59660) of the Ministry of Science and ICT.

CROSS-REFERENCE TO RELATED APPLICATION

This application claims priority to Korean Patent Application No. 10-2021-0010201, filed on Jan. 25, 2021, and all the benefits accruing therefrom under 35 U.S.C. § 119, the contents of which in its entirety are herein incorporated by reference.

BACKGROUND

1. Field

The present disclosure relates to an atomizer, and more particularly, to a mesh type atomizer for atomizing a liquid into nanometer-level fine particles using a porous thin film including holes having nanometer diameters.

2. Description of the Related Art

A medical nebulizer is equipped with an atomizer for atomizing liquid medicine into fine particles floating in the air that a patient can inhale through the respiratory system. The atomizer may be largely classified into an air jet atomizer, an ultrasonic wave atomizer and a vibrating mesh atomizer according to the liquid atomization mechanism. The air jet atomizer sprays a jet of compressed air to the surface of liquid medicine located at the base and forces the medicine floating in the air through nozzles, and the ultrasonic wave atomizer emits ultrasonic waves to the surface of liquid medicine to give vibrations and forces the medicine floating in the air through nozzles. Since the air jet or ultrasonic wave atomizer pushes droplets by mechanical striking, the atomized particle size is not uniform and it is difficult to reduce droplets to a predetermined size or less, resulting in a low rate of absorption into the respiratory system.

The vibrating mesh atomizer reduces liquid medicine to fine particles through a mesh having very small holes, and causes vibration to release the particles into the air. The common vibrating mesh atomizer includes a mesh thin film for producing very small droplets and an ultrasonic transducer for giving ultrasonic vibrations to the mesh thin film to cause the ejection of the droplets. The vibrating mesh atomizer has a uniform hole diameter of the mesh, and thus can form uniform particles compared to the air jet or ultrasonic wave atomizer.

The mesh thin film is usually made through laser drilling (drilling of holes in the thin film by micro-laser irradiation), and a minimum size of hole that can be machined using a laser is about 2.5 micrometers. The size of particle atomized through the mesh is at least twice larger than the mesh hole size, so the atomized particle is a minimum of 5 micrometers in size.

Japanese Patent No. 6415953 discloses a mesh manufactured by forming holes having the diameter of 3 to 25 micrometers in a substrate through laser drilling, for use in a liquid atomizer.

Most of medical nebulizers have been developed for asthma patients and medicines for asthma patients are designed to be absorbed into larynx. Since the size of a particle that can be absorbed in larynx is about 4.7 to 7 micrometers, the existing atomizers that produce droplets of about 5 micrometers can be sufficiently used.

However, in the case of lung disease patients, it is required that medicine is absorbed into lungs to obtain the medicine's definite effects, and the size of a particle that can be absorbed in lungs is about 0.65 to 1.1 micrometers (i.e., a nanometer level) in size, which is smaller than the size of a particle that can be absorbed in larynx or other organs. However, the existing atomizer mesh manufactured by laser drilling is impossible to produce nanometer sized particles due to the technical limitation, and thus cannot be used for the treatment of lung diseases.

SUMMARY

The present disclosure is directed to providing a mesh type atomizer for atomizing a liquid into nanometer sized fine particles using a porous thin film as a mesh and a method for manufacturing the same.

A mesh type atomizer according to an embodiment includes a porous thin film having a multi-hole structure, a metal layer covering a remaining area except a nozzle area in which droplets are sprayed through the holes on a surface of the porous thin film, and an ultrasonic transducer to output ultrasonic waves to vibrate the porous thin film.

According to an embodiment, the hole in the remaining area except the nozzle area may be, at least in part, filled with a metal material.

According to an embodiment, the hole of the porous thin film may be a few nanometers to a few micrometers in diameter.

According to an embodiment, the porous thin film is anodic aluminum oxide.

According to an embodiment, the nozzle area may include at least one hole, and the droplet sprayed through the nozzle area may be a few nanometers to a few micrometers in diameter.

According to an embodiment, a distance between the nozzle area and an adjacent nozzle area may be set to prevent the droplets sprayed in each nozzle area from merging.

A method for manufacturing a mesh type atomizer according to an embodiment includes providing a porous thin film having a multi-hole structure, forming a photosensitive layer in a nozzle area in which droplets are to be sprayed through the holes on a surface of the porous thin film, depositing a metal layer on the porous thin film and the photosensitive layer, removing the photosensitive layer from the porous thin film, and combining an ultrasonic transducer with the porous thin film.

According to an embodiment, the method for manufacturing a mesh type atomizer may further include, after depositing the metal layer on the porous thin film and the photosensitive layer, connecting an electroplating metal material to the metal layer, and growing a metal material in the hole of a remaining area except the nozzle area through electroplating.

Using the atomizer according to an embodiment, a liquid may be atomized into nanometer-level fine particles using the porous thin film including nanometer sized holes. As the size of particles that can be formed by the existing mesh type atomizers manufactured by laser drilling is a few micrometers or more, absorption of liquid medicine into lungs is disallowed. In contrast, according to an embodiment, it is possible to atomize liquid medicine into nanometer sized particles which can be directly absorbed into lungs, and thus it can be advantageously used for the treatment of lung diseases.

Additionally, the sprayed droplet size may be precisely adjusted by setting the shape, size and interval of the nozzle according to the atomizer manufacturing process, and the strength of the mesh may be selectively increased by growing the metal material in the hole of the porous thin film through electroplating.

The embodiments may be applied in various technical fields including, but not limited to, medical fields. For example, when applied to automotive engines, it is possible to increase the complete combustion efficiency of fuel by spraying fine fuel particles compared to the conventional art, and when applied in chemical fields, it may be used to generate or filter nanometer sized particles.

BRIEF DESCRIPTION OF THE DRAWINGS

The following is a brief introduction to necessary drawings in the description of the embodiments to describe the technical solutions of the embodiments of the present disclosure or the existing technology more clearly. It should be understood that the accompanying drawings are for the purpose of describing the embodiments of the present disclosure and are not intended to be limiting of the present disclosure. Additionally, for clarity of description, illustration of some elements in the accompanying drawings may be exaggerated and omitted.

DETAILED DESCRIPTION

Figure 1:
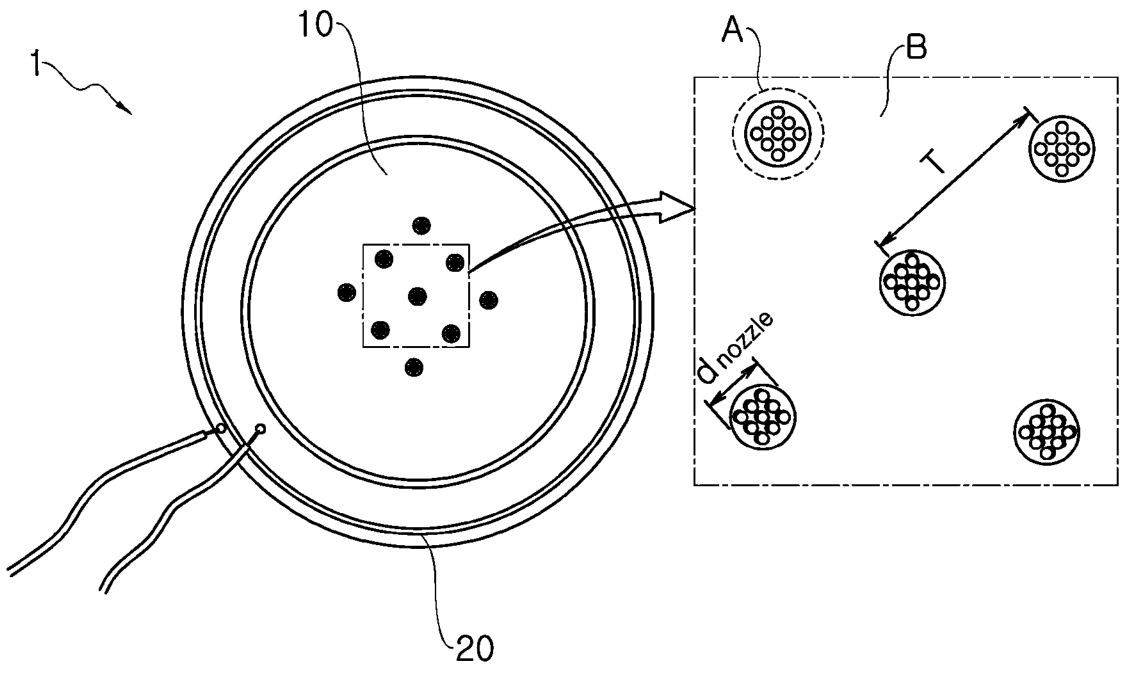
FIG. 1 shows the structure of a mesh type atomizer according to an embodiment.

The following detailed description of the present disclosure is made with reference to the accompanying drawings, in which particular embodiments for practicing the present disclosure are shown for illustration purposes. These embodiments are described in sufficiently detail for those skilled in the art to practice the present disclosure. It should be understood that various embodiments of the present disclosure are different but do not need to be mutually exclusive. For example, particular shapes, structures and features described herein in connection with one embodiment may be embodied in other embodiment without departing from the spirit and scope of the present disclosure. It should be further understood that changes may be made to the positions or placement of individual elements in each disclosed embodiment without departing from the spirit and scope of the present disclosure. Accordingly, the following detailed description is not intended to be taken in limiting senses, and the scope of the present disclosure, if appropriately described, is only defined by the appended claims along with the full scope of equivalents to which such claims are entitled. In the drawings, similar reference signs denote same or similar functions in many aspects.

Hereinafter, the embodiments will be described in detail with reference to the accompanying drawings, but the scope of protection is not restricted or limited by the embodiments.

FIG. 1 shows the structure of a mesh type atomizer according to an embodiment. Referring to FIG. 1, the atomizer 1 according to an embodiment includes a mesh structure 10 for breaking up a liquid into fine particles and an ultrasonic transducer 20 for vibrating the mesh structure 10 using ultrasonic waves. The mesh structure 10 may be divided into at least one nozzle area A where droplets are sprayed and a remaining area B covered with a metal layer. Although not shown for simplification of description, the mesh type atomizer may further include essential or optional elements for its operation.

Figure 2:
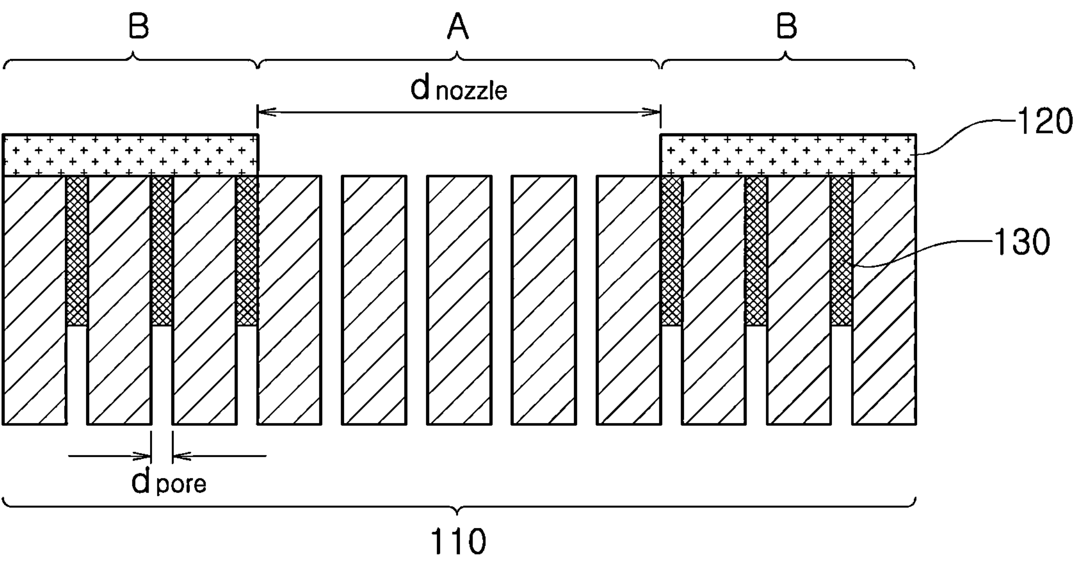
FIG. 2 is a cross-sectional view of a mesh structure used in a mesh type atomizer according to an embodiment.

FIG. 2 is a cross-sectional view of the mesh structure used in the mesh type atomizer according to an embodiment. Referring to FIG. 2, the mesh structure includes a porous thin film 110 having a multi-hole structure and a metal layer 120 that covers the remaining area B except the nozzle area A where droplets are sprayed through the holes on the surface of the porous thin film 110. The hole in the remaining area B except the nozzle area A may be, at least in part, filled with a metal material 130.

Figure 3:
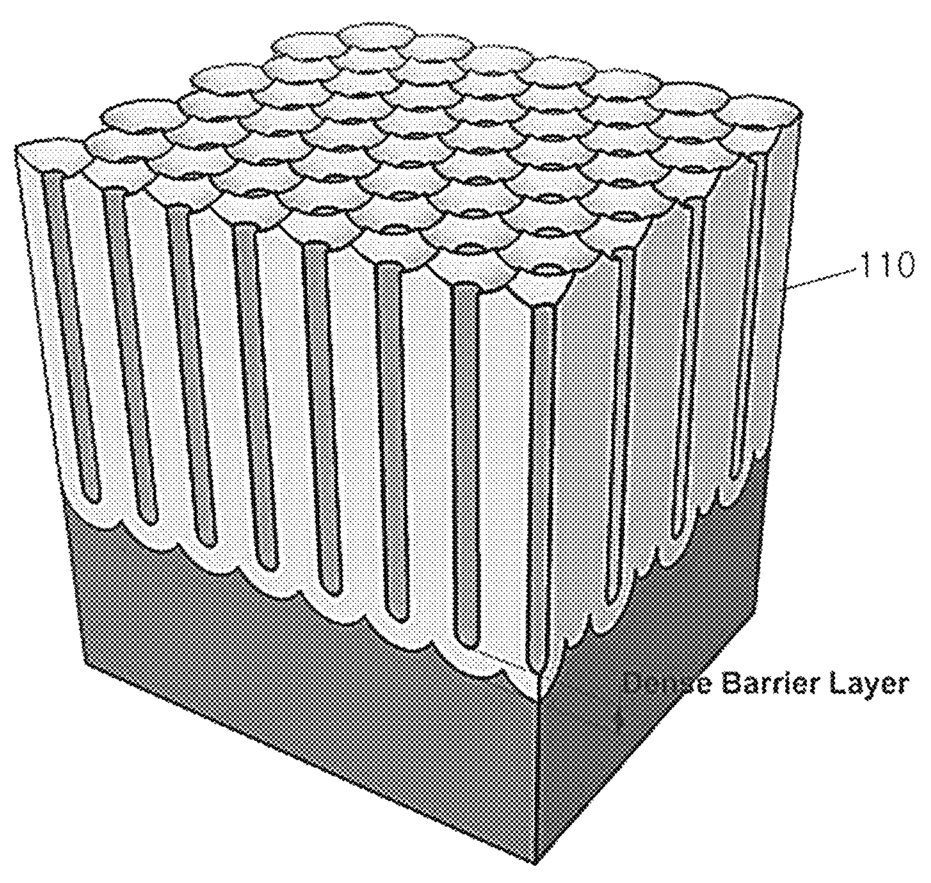
FIG. 3 shows a porous thin film used to manufacture a mesh structure according to an embodiment.

FIG. 3 shows the porous thin film used to manufacture the mesh structure according to an embodiment. According to the embodiment, the porous thin film 110 includes a plurality of holes having very small diameters of a few nanometers to a few micrometers. For example, anodic aluminum oxide having nanometer sized holes may be used. The type of the porous thin film or the size of the hole is not limited thereto and various types of porous thin films having holes of various sizes may be used.

Referring to FIG. 2, the metal layer 120 covers the remaining area B except the nozzle area A where droplets are sprayed through the holes on the surface of the porous thin film 110. Since the remaining area B is blocked by the metal layer 120, a liquid is only sprayed through the nozzle area A. The nozzle area A includes at least one hole, and the droplet sprayed through the nozzle area A has a very small size on the level of a few nanometers to a few micrometers. The droplet size may vary depending on the number of holes in the nozzle area A and the diameter of each hole. The size of a droplet passing through a hole is about twice larger than the diameter of the hole, and may become larger when the droplet and droplets of adjacent holes merge, so the actually sprayed droplet size is not equal to the hole size, but the sprayed droplet size may be adjusted by adjusting the size of the nozzle area in the mesh manufacturing process. For example, nanometer sized droplets may be formed by using the porous thin film (AAO) including nanometer-level holes and limiting the size of the nozzle.

According to an embodiment, the holes in the area B other than the nozzle may be partially filled with the metal material 130 to increase the strength of the mesh or selectively adjust the ultrasonic resonant frequency. The metal material in the hole may be grown using electroplating.

Referring back to FIG. 1, the distance between a nozzle area and its adjacent nozzle area is indicated in T, and the diameter of the nozzle area is indicated in $d_{nozzle}$. The distance T between the nozzle areas may be set to an optimal distance to prevent droplets sprayed in each nozzle area from merging. The diameter $d_{nozzle}$ of the nozzle area may be set, taking the sprayed droplet size into account. That is, the diameter may be set to a larger value to make droplets larger, or may be set to a smaller value to make droplets smaller.

The ultrasonic transducer 20 outputs ultrasonic waves to vibrate the mesh structure 10. As shown in FIG. 1, the ring type ultrasonic transducer 20 attached to the edge of the mesh structure 10 may be used. The mesh structure 10 vibrates by the ultrasonic waves outputted from the ultrasonic transducer 20, and atomizes a liquid into fine particles (preferably, droplets having nanometer diameters).

Hereinafter, a method for manufacturing a mesh type atomizer according to an embodiment will be described with reference to FIGS. 4A to 4E.

Figure 4A:
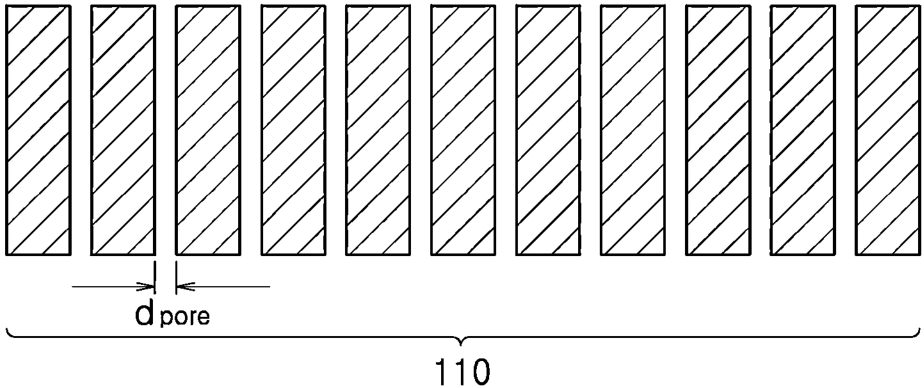
FIGS. 4A to 4E are diagrams for describing a method for manufacturing a mesh type atomizer according to an embodiment.

According to an embodiment, first, a porous thin film 110 having a multi-hole structure is provided as shown in FIG. 4A. The porous thin film 110 includes a plurality of holes, and the diameter $d_{pore}$ of each hole may be a few nanometers to a few micrometers. For example, anodic aluminum oxide having nanometer-sized holes may be used as the porous thin film 110.

Figure 4B:
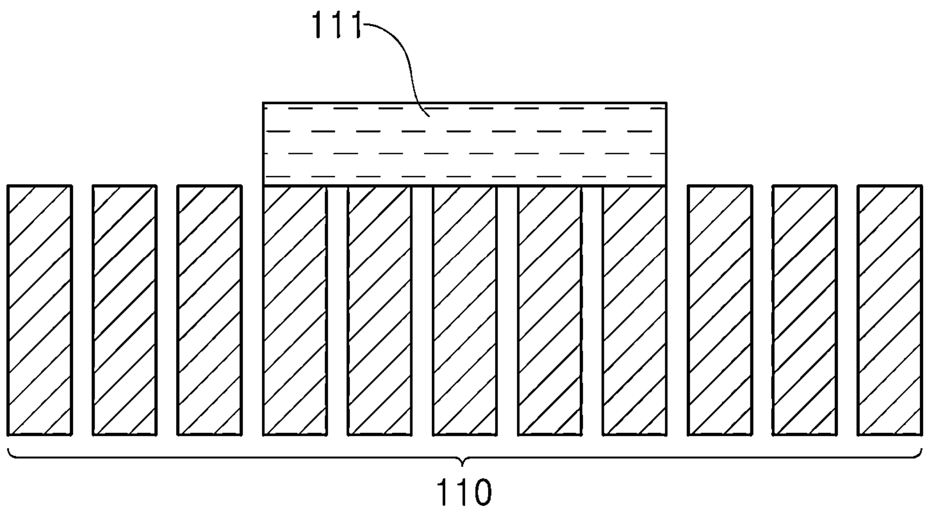

Subsequently, a photosensitive layer 111 is formed on a part of the surface of the porous thin film 110 as shown in FIG. 4B. An area having the photosensitive layer is a nozzle area where droplets will be sprayed through the holes.

Figure 4C:
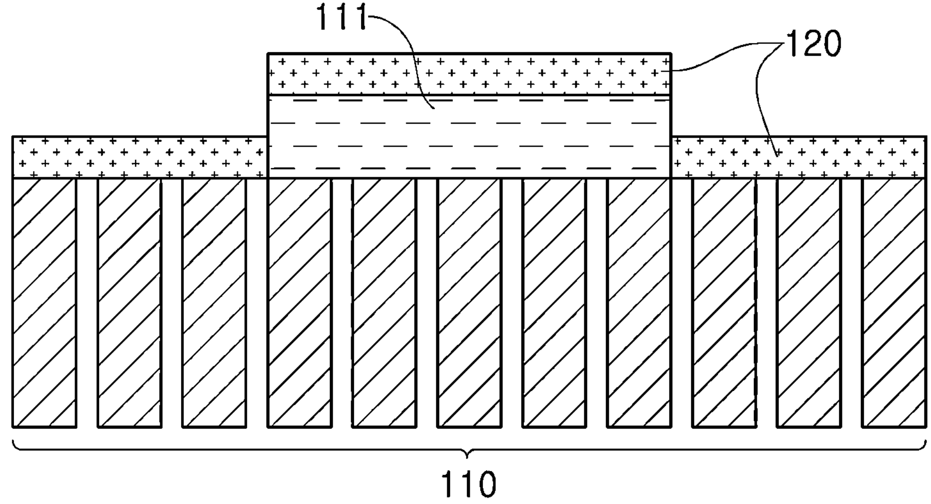

Subsequently, a metal layer 120 is deposited, covering the porous thin film 110 and the photosensitive layer 111 as shown in FIG. 4C. There is no limitation as to the type of the metal material of which the metal layer 120 is made, and the metal layer 120 may be deposited using the existing thin film deposition process, for example, chemical vapor deposition (CVD) and physical vapor deposition (PVD).

Figure 4D:
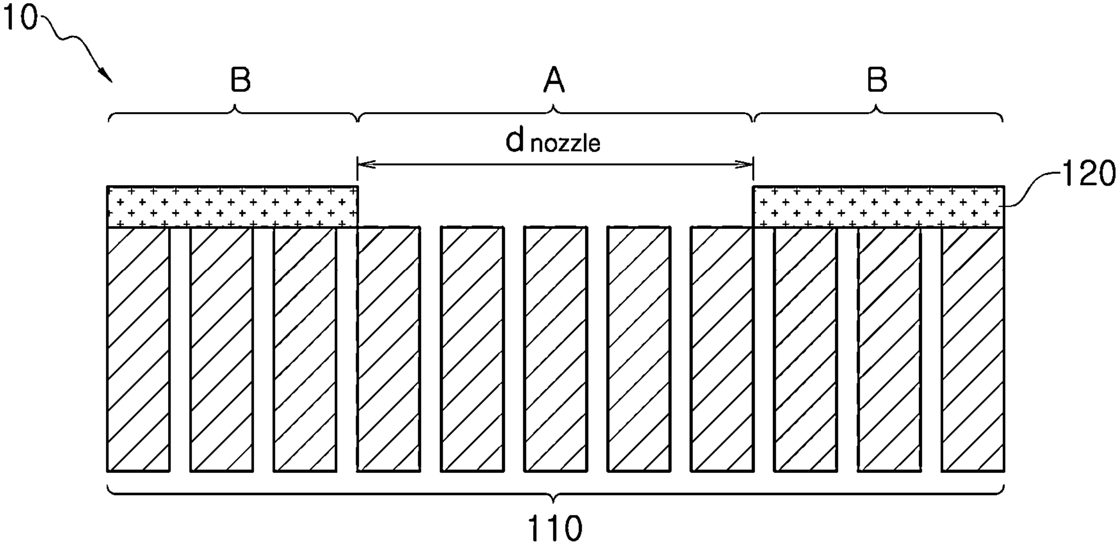

Subsequently, the photosensitive layer 111 is removed from the porous thin film 110 to form a mesh structure. In the mesh structure, as shown in FIG. 4D, the area A in which the photosensitive layer 111 has been formed is exposed and the remaining area B is covered with the metal layer 120. The area A is the nozzle area where droplets are sprayed through the holes.

Figure 4E:
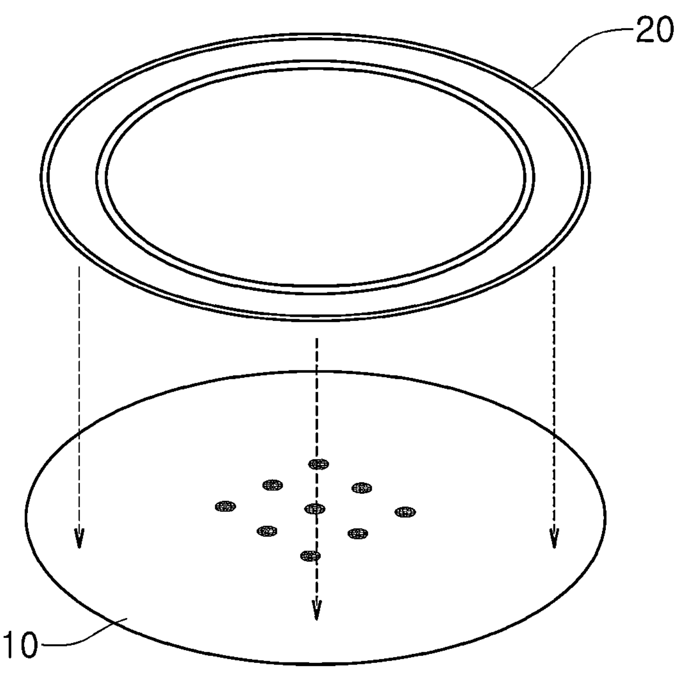

The mesh structure 10 is formed through the process of FIGS. 4A to 4D, and an ultrasonic transducer 20 is combined with the mesh structure 10 to manufacture an atomizer according to an embodiment as shown in FIG. 4E. As shown in FIG. 4E, the ring type ultrasonic transducer 20 may be used.

Figure 5A:
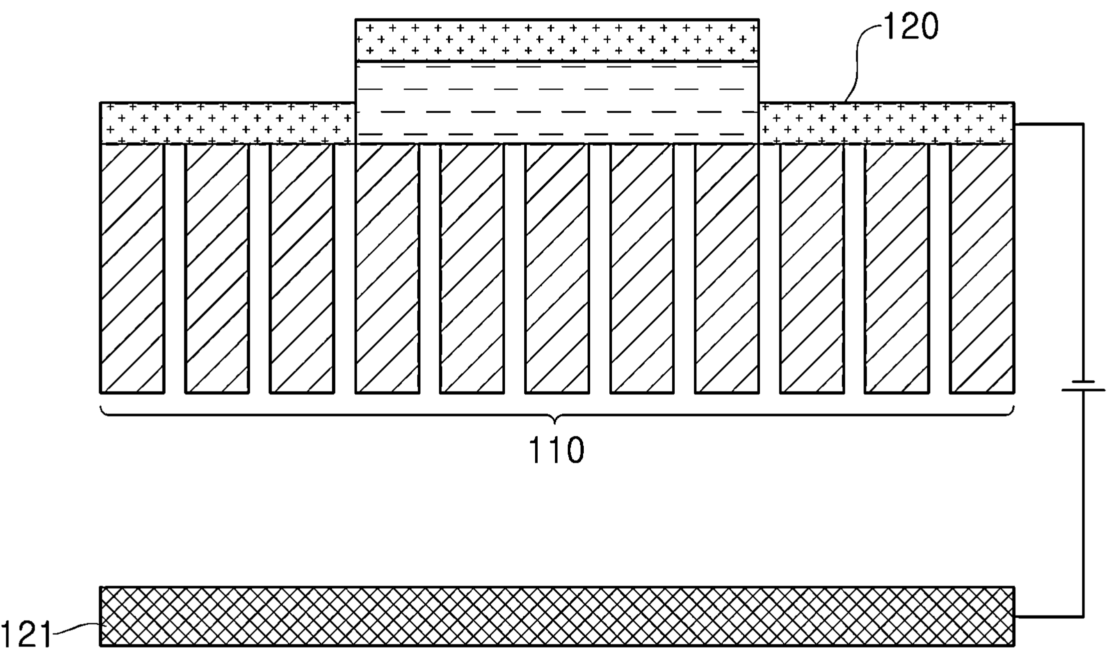
FIGS. 5A and 5B are diagrams for describing a method for manufacturing a mesh structure with increased strength according to an embodiment.
Figure 5B:
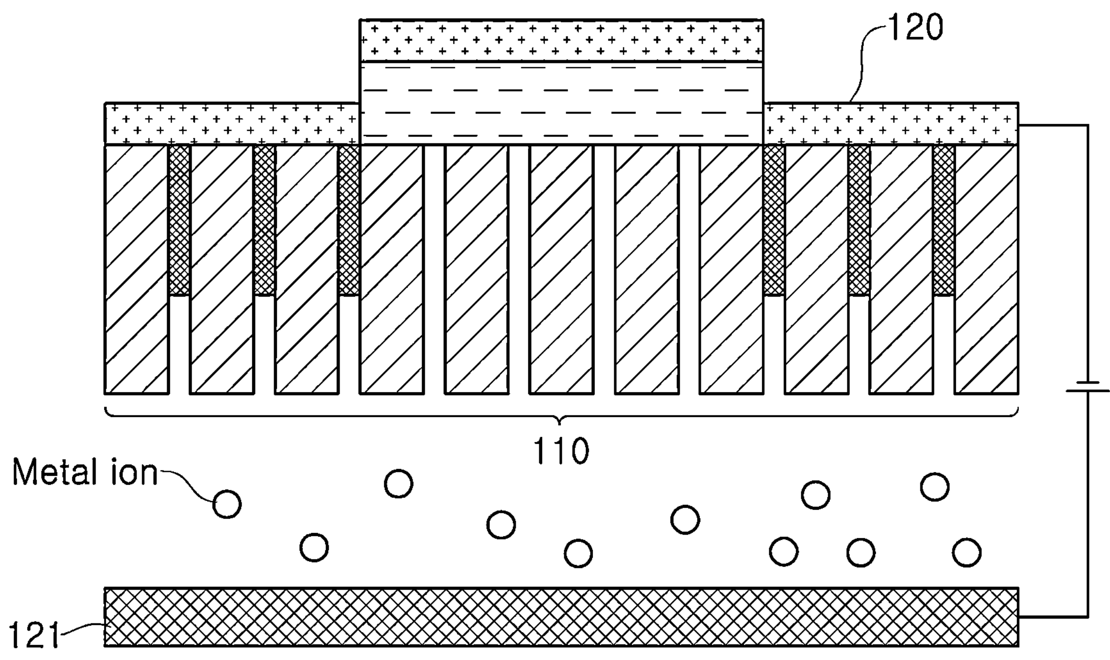

FIGS. 5A and 5B are diagrams for describing a method for manufacturing a mesh structure with increased strength according to an embodiment.

In this embodiment, the process of FIGS. 4A to 4C is performed in the same way as the previous embodiment. After the step of depositing the metal layer 120 on the porous thin film 110 and the photosensitive layer 111 in FIG. 4C, the metal layer 120 and an electroplating metal material 121 are connected through an electrode as shown in FIG. 5A. The type of the electroplating metal material 121 may vary depending on the type of metal of which the metal layer 120 is made.

When the metal layer 120 and the electroplating metal material 121 are connected with the electrode, a metal material 130 is grown in the hole through oxidation and reduction of metal ions in an electrolyte as shown in FIG. 5B. In this instance, the metal material is not grown in the area having the photosensitive layer 111 (later formed as the nozzle area), and the metal material in the hole is only grown in the remaining area. Accordingly, it is possible to increase the strength of the mesh structure while not inhibiting the liquid atomization function of the porous thin film.

Figure 6A:
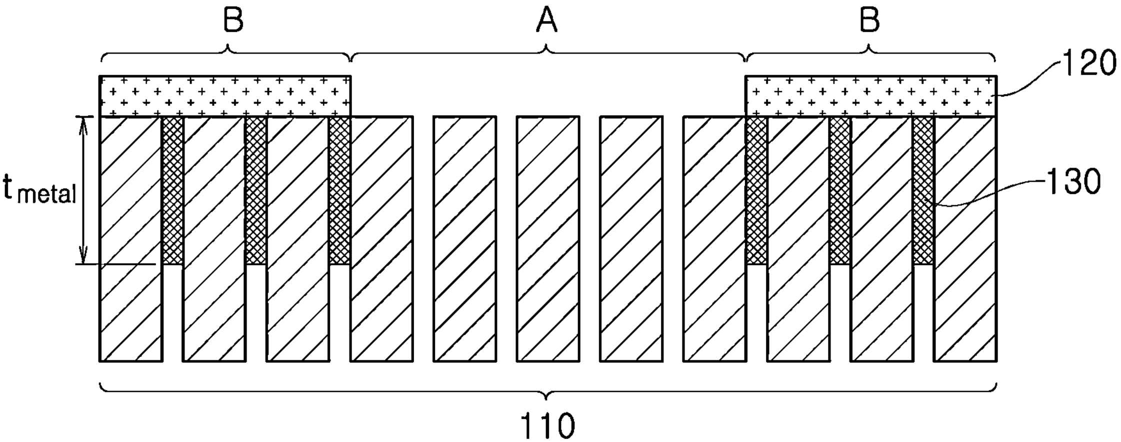
FIGS. 6A and 6B are cross-sectional views of a mesh structure with increased strength according to an embodiment.
Figure 6B:
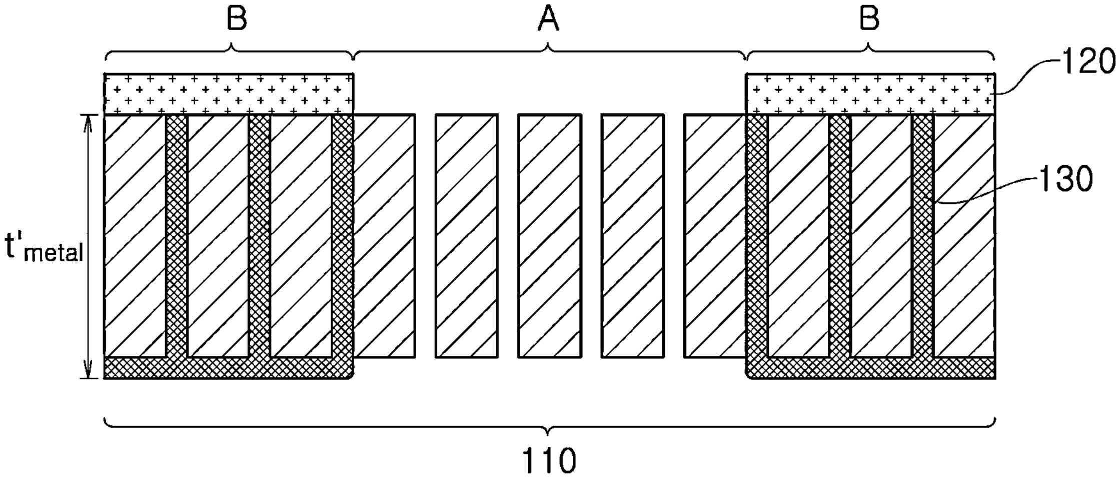

FIGS. 6A and 6B are cross-sectional views of the mesh structure with increased strength according to an embodiment. As described above, the metal material 130 may be grown in the hole of the porous thin film 110 through electroplating, and the height $t_{metal}$ of the metal material 130 may be adjusted by adjusting the electroplating process time. FIG. 6A shows that the hole is partially filled with the metal material 130, and FIG. 6B shows that the hole is fully filled with the metal material 130. The strength of the mesh structure may be adjusted by selectively adjusting the thickness of the metal material, thereby selectively adjusting the ultrasonic resonant frequency.

Figure 7:
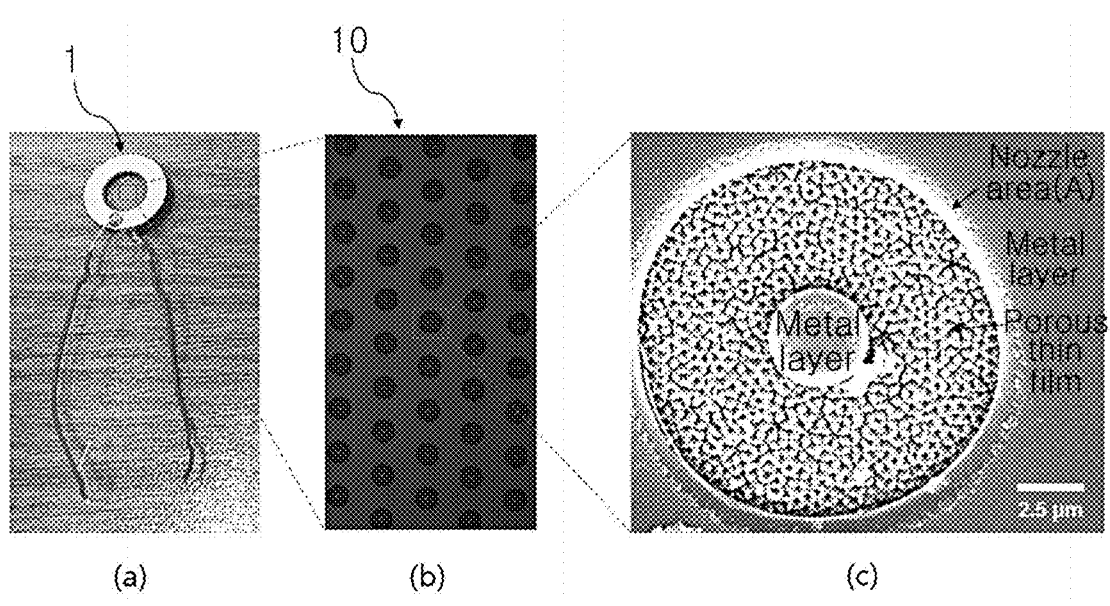
FIG. 7 shows a photographic image of a mesh type atomizer manufactured according to an embodiment and a scanning electron microscope (SEM) image of a nozzle area made of a porous thin film.

FIG. 7 shows a photographic image of the mesh type atomizer manufactured according to an embodiment and a scanning electron microscope (SEM) image of the nozzle area having the porous thin film structure. In FIG. 7, (A) shows the whole structure of the mesh type atomizer 1. (B) is an enlarged photographic image of the mesh structure 10 of the atomizer, and (C) is an enlarged photographic image of one of the nozzle areas A included in the mesh structure. As can be seen in (C), one nozzle area includes a plurality of nanometer sized holes through which fine droplets having the size of a few nanometers are sprayed. As shown, the area other than the nozzle area is covered with the metal layer and droplets are not sprayed there.

According to the mesh type atomizer described hereinabove, it is possible to atomize a liquid into nanometer-level fine particles using the porous thin film including the nanometer sized holes. It is possible to precisely adjust the sprayed droplet size by setting the shape, size and interval of the nozzle in the manufacturing process, and it is possible to selectively increase the strength of the mesh by growing the metal material in the hole of the porous thin film through electroplating. It is possible to form much smaller droplets compared to the existing mesh drilled by laser drilling, and it can be used in various technical fields including medical nebulizers used to administer fine drug particles, fuel injection systems of automotive engines, filters or the like.

While the present disclosure has been hereinabove described with reference to the embodiments, those skilled in the art will understand that various modifications and changes may be made thereto without departing from the spirit and scope of the present disclosure defined in the appended claims.

What is claimed is:

1. A mesh type atomizer, comprising:

a porous thin film having a multi-hole structure and comprising a nozzle area and a remaining area outside of the nozzle area, the porous thin film having a plurality of holes in the nozzle area and the remaining area, the nozzle area being an area of the porous thin film where droplets are sprayed through the holes;

a metal layer covering the remaining area on a surface of the porous thin film and not covering the nozzle area; and an ultrasonic transducer to output ultrasonic waves to vibrate the porous thin film, wherein at least some of the holes in the remaining area are filled with a metal material grown in the holes through electroplating.

2. The mesh type atomizer according to claim 1, wherein all of the holes in the remaining area are filled with the metal material.

3. The mesh type atomizer according to claim 1, wherein each of the holes of the porous thin film has a diameter between a few nanometers and a few micrometers.

4. The mesh type atomizer according to claim 3, wherein the porous thin film is anodic aluminum oxide.

5. The mesh type atomizer according to claim 1, wherein the nozzle area includes at least one hole, and the droplets sprayed through the nozzle area have a diameter between a few nanometers and a few micrometers.

6. The mesh type atomizer according to claim 5, wherein a distance between the nozzle area and an adjacent nozzle area is set to prevent the droplets sprayed in each nozzle area from merging.

7. The mesh type atomizer of claim 1, wherein the metal material extends only partially through the holes of the remaining area.

8. The mesh type atomizer of claim 1, wherein the metal material extends through an entirety of the holes of the remaining area.

9. The mesh type atomizer of claim 1, wherein the ultrasonic transducer is a ring-type ultrasonic transducer that surrounds an entirety of the porous thin film.

* * * * *